(12) United States Patent
Papisov (10) Patent No.: US 8,106,098 B2
(45) Date of Patent: Jan. 31, 2012

(54) PROTEIN CONJUGATES WITH A WATER-SOLUBLE BIOCOMPATIBLE, BIODEGRADABLE POLYMER

(75) Inventor: Mikhail I. Papisov, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 1259 days.

(21) Appl. No.: 11/651,437

(22) Filed: Jan. 9, 2007

(65) Prior Publication Data

US 2008/0019940 A1     Jan. 24, 2008

Related U.S. Application Data

(63) Continuation-in-part of application No. 10/622,998, filed on Jul. 18, 2003, now Pat. No. 7,160,924, and a continuation-in-part of application No. 10/994,213, filed on Nov. 19, 2004, which is a continuation of application No. 09/634,320, filed on Aug. 9, 2000, now Pat. No. 6,822,086.

(60) Provisional application No. 60/397,509, filed on Jul. 19, 2002, provisional application No. 60/147,919, filed on Aug. 9, 1999.

(51) Int. Cl.
    *A61K 38/00*     (2006.01)
(52) U.S. Cl. ........ 514/693; 514/694; 514/886; 514/909; 525/54.1; 525/401; 525/403; 525/405; 525/462; 424/78.05
(58) Field of Classification Search .................. 514/693, 514/909, 694, 886.4, 886; 424/78.05; 525/54.1, 525/401, 403, 405, 462
    See application file for complete search history.

(56) References Cited

U.S. PATENT DOCUMENTS

| | | | |
|---|---|---|---|
| 4,695,463 A | 9/1987 | Yang et al. | |
| 4,695,623 A | 9/1987 | Stabinsky | |
| 4,703,008 A | 10/1987 | Lin | |
| 4,810,643 A | 3/1989 | Souza | |
| 4,897,471 A | 1/1990 | Stabinsky | |
| 4,999,291 A | 3/1991 | Souza | |
| 5,075,222 A | 12/1991 | Hannum et al. | |
| 5,372,808 A | 12/1994 | Blatt et al. | |
| 5,441,868 A | 8/1995 | Lin | |
| 5,541,293 A | 7/1996 | Stabinsky | |
| 5,547,933 A | 8/1996 | Lin | |
| 5,574,142 A | 11/1996 | Meyer, Jr. et al. | |
| 5,578,709 A | 11/1996 | Woiszwillo | |
| 5,581,476 A | 12/1996 | Osslund | |
| 5,582,172 A | 12/1996 | Papisov et al. | |
| 5,582,823 A | 12/1996 | Souza | |
| 5,612,037 A | 3/1997 | Huebner et al. | |
| 5,618,698 A | 4/1997 | Lin | |
| 5,621,080 A | 4/1997 | Lin | |
| 5,624,803 A | 4/1997 | Noonberg et al. | |
| 5,811,510 A | 9/1998 | Papisov | |
| 5,817,343 A | 10/1998 | Burke | |
| 5,824,784 A | 10/1998 | Kinstler et al. | |
| 5,863,990 A | 1/1999 | Papisov | |
| 5,958,398 A | 9/1999 | Papisov | |
| 5,981,719 A | 11/1999 | Woiszwillo et al. | |
| 6,048,837 A | 4/2000 | Friedman et al. | |
| 6,057,431 A | 5/2000 | Ishihara et al. | |
| 6,090,925 A | 7/2000 | Woiszwillo et al. | |
| 6,294,170 B1 | 9/2001 | Boone et al. | |
| 6,506,559 B1 | 1/2003 | Fire et al. | |
| 6,610,841 B1 | 8/2003 | Warren | |
| 6,822,086 B1 * | 11/2004 | Papisov ....................... 536/24.2 |
| 7,160,924 B2 | 1/2007 | Kinstler et al. | |
| 7,220,414 B2 | 5/2007 | Brocchini et al. | |
| 7,270,808 B2 | 9/2007 | Cheng et al. | |
| 7,785,618 B2 | 8/2010 | Elmaleh et al. | |
| 7,790,150 B2 | 9/2010 | Papisov et al. | |
| 2006/0019911 A1 | 1/2006 | Papisov | |
| 2006/0058513 A1 | 3/2006 | Papisov et al. | |
| 2006/0069230 A1 | 3/2006 | Papisov | |
| 2010/0150832 A1 | 6/2010 | Papisov | |

FOREIGN PATENT DOCUMENTS

| | | |
|---|---|---|
| AU | 9173636 B | 5/1994 |
| DE | 4219626 | 12/1993 |
| EP | 0280474 | 8/1988 |
| EP | 0 325 270 * | 7/1989 |
| EP | 0325270 | 7/1989 |
| FR | 2706772 | 12/1994 |
| GB | 1440626 | 6/1976 |
| WO | WO 91/05795 | 5/1991 |
| WO | WO 91/08285 | 6/1991 |
| WO | WO 91/14696 | 10/1991 |
| WO | WO 91/17184 | 11/1991 |
| WO | WO 92/16221 | 10/1992 |
| WO | WO 92/17505 | 10/1992 |
| WO | WO 93/21946 | 11/1993 |
| WO | WO 94/06457 | 3/1994 |
| WO | WO 94/17185 | 8/1994 |
| WO | WO 94/20517 | 9/1994 |
| WO | WO 94/21235 | 9/1994 |

(Continued)

OTHER PUBLICATIONS

U.S. Appl. No. 60/397,509, Kinstler et al.
Anderson, R.D., et al., "DNA Sequence Specificity of Doxorubicin-induced Mutational Damage in uvrB-*Escherichia coli*", *Cancer Research*, 51:3930-3937 (1991).
Bendele, et al., "Short Communication: Renal Tubular Vacuolation in Animals Treated with Polyethylene-Glycol-Conjugated Proteins," *Toxicological Sciences* 42, 152-157 (1998).
Binaschi, M., et al., "Relationship between Lethal Effects and Topoisomerase II-Mediated Double-Stranded DNA Breaks Produced by Anthracyclines with Different Sequence Specificity" *Molecular Pharmacology*, 51:1053-1059 (1997).
Borgnetto, M.E., et al., "Drug-specific Sites of Topoisomerase II DNA Cleavage in *Drosophila* Chromatin: Heterogeneous Localization and Reversibility", *Cancer Research*, 56:1855-1862 (1996).

(Continued)

*Primary Examiner* — Irina S Zemel
(74) *Attorney, Agent, or Firm* — Brenda Herschbach Jarrell; Kristen C. Buteau; Choate, Hall & Stewart LLP (57) ABSTRACT

The present invention broadly relates to the field of protein modification, and, more specifically, to conjugates of proteins or analogs thereof to a water-soluble biocompatible polymer and methods of making and using the same.

6 Claims, 2 Drawing Sheets

FOREIGN PATENT DOCUMENTS

| | | |
|---|---|---|
| WO | WO 94/21275 | 9/1994 |
| WO | WO 95/17206 | 6/1995 |
| WO | WO 96/05309 | 2/1996 |
| WO | WO 96/22793 | 8/1996 |
| WO | WO 96/30536 | 10/1996 |
| WO | WO 96/40912 | 12/1996 |
| WO | WO 97/00128 | 1/1997 |
| WO | WO 97/01010 | 1/1997 |
| WO | WO 97/01331 | 1/1997 |
| WO | WO 97/06816 | 2/1997 |
| WO | WO 97/18833 | 5/1997 |
| WO | WO 97/23614 | 7/1997 |
| WO | WO 97/38014 | 10/1997 |
| WO | WO 98/00172 | 1/1998 |
| WO | WO 98/08512 | 3/1998 |
| WO | WO 98/28427 | 7/1998 |
| WO | WO 99/30561 | 6/1999 |
| WO | WO 00/21574 | 4/2000 |
| WO | WO 00/50050 | 8/2000 |
| WO | WO 00/78285 | 12/2000 |
| WO | WO 00/78355 A2 | 12/2000 |
| WO | WO 01/07486 A1 | 2/2001 |
| WO | WO 01/10468 * | 2/2001 |
| WO | WO 01/10468 A2 | 2/2001 |
| WO | WO 03/059988 A2 | 7/2003 |
| WO | WO 2004/009774 | 1/2004 |

OTHER PUBLICATIONS

Bruneel D. et al. "Chemical modification of pullulan: 3. Succinoylation" Polymer, Elsevier Science Publishers B.V, GB, vol. 35, No. 12, Jun. 1, 1994, pp. 2656-2658.
Capranico, G., et al., "Change of the Sequence Specificity of Daunorubicin-stimulated Topoisomerase II DNA Cleavage by Epimerization of the Amino Group of the Sugar Moiety", *Cancer Research*, 55:312-317 (1995).
Capranico, G., et al., "Conformational D6 rug Determinants of the Sequence Specificity of Drug-stimulated Topoisomerase II DNA Cleavage", *J. Mol. Biol.*, 235:1218-1230 (1994).
Capranico, G., et al., "Unique Sequence Specificity of Topoisomerase II DNA Cleavage Stimulation and DNA Binding Mode of Streptonigrin", *J. Biol. Chem.*, 269(40):25004-25009 (1994).
Capranico, G., et al., "Similar Sequence Specificity of Mitoxantrone and VM-26 Stimulation of in Vitro DNA Cleavage by Mammalian DNA Topoisomerase II", *Biochemistry*, 32:3038-3046 (1993).
Cervigni S. et al. "Synthesis of Glycopeptides and Lipopeptides by Chemoselective Ligation" *Angew. Chem. Int. Ed. Egl.* 1996, 35, No. 11, pp. 1230-1232.
Chaires, J.B., et al., "Site and Sequence Specificity of the Daunomycin-DNA Interaction", *Biochemistry*, 26:8227-8236 (1987).
Chollet, A., "Selective Attachment of Oligonucleotides to Interleukin 1β and Targeted Delivery to Cells", *Nucleosides and Nucleotides*, 9(7):957-966 (1990).
Conover, et al., "Physiological Effect of Polyethylene Glycol Conjugation on Stroma-Free Bovine Henoglobin in the Conscious Dog After Partial Exchange Transfusion," *Artificial Organs* 1997, 21(5):369-378.
Cornarotti, M., et al., "Drug Sensivity and Sequence Specificity of Human Recombinant DNA Topoisomerases IIα (p170) and IIβ (p180)", *Molecular Pharmacology*, 50:1463-1471 (1996).
Cullinane, C., et al., "The DNA Sequence Specificity of Cyanomorpholinoadriamycin", *FEBS*, 293(1)(2):195-198 (1991).
Cullinane, C., et al., "Formation of adriamycin—DNA adducts in vitro", *Nucleic Acid Research*, 22(12):2296-2303 (1994).
Cullinane, C. and Phillips, D.R., "Sequence Specificity of (Cyanomorpholino) adriamycin Adducts in Human Cells", *Biochemistry*, 33:6207-6212 (1994).
Cummings, J., et al., "Determination of Covalent Binding to Intact DNA, RNA, and Oligonucleotides by Intercalating Anticancer Drugs Using High-Performance Liquid Chromatography. Studies with Doxorubicin and NADPH Cytochrome P-450 Reductase", *Analytical Biochemistry*, 194:146-155 (1991).
D'Incalci, M., "DNA-topoisomerase inhibitors", *Current Opinion in Oncology*, 5:1023-1028 (1993).
Dabrowiak, J.C., "MiniReview: Sequence Specificity of Drug-DNA Interactions", *Life Sciences*, 32:2915-2931 (1983).
Database PUBMED, Accession No. 9404651, Bonora G.M. et al., "Synthesis and Characterization of High-Molecular Mass Polyethylene Glycol-Conjugated Oligonucleotides," [online], [retrieved from MEDLINE on Jan. 13, 2003], (1997).
Database PUBMED, Accession No. 9327134, Katayose, S. et al., "Water-Soluble Polyion Complex Associates of DNA and Poly(ethylene glycol)-Poly(L-lysine) Block Copolymer," [online], [retrieved from MEDLINE on Jan. 13, 2003], (1997).
Database PUBMED, Accession No. 7984434. Jaschke, A. et al., "Synthesis and Properties of Oligodeoxyribonucleotide-Polyethylene Glycol Conjugates," [online], [retrieved from MEDLINE on Jan. 13, 2003], (1994).
Database PUBMED, Accession No. 7550108, Kawaguchi, T. et al., "Stability, Specific Binding Activity, and Plasma Concentration in Mice of and Oligodeoxynucleotide Modified at 5'-Terminal with Poly(ethylene glycol)", [online], [retrieved from MEDLINE on Jan. 13, 2003], (1995).
Database PUBMED, Accession No. 8747481. Wang, J. et al., "Use of a Polytheylene Glycol-Peptide Conjugate in a Competition Gel Shift Assay for Screening Potential Antagonists of HIV-1 Tat Protein Binding to TAR RNA," [online], [retrieved from MEDLINE on Jan. 13, 2003], (1995).
Duncan, R. Polymer-Drug Conjugates. In: Handbook of Anticancer Drug Development, D. Budman, H. Calvert, and E. Rowinsky (Eds.), Lippincott, Williams & Wilkins Philadelphia (2003) pp. 239-260.
Endo et al. Nature of Linkage and Mode of Action of Methotrexate Conjugated with Antitumor Antibodies: Implications for Future Preparation of Conjugates. *Cancer Research* 48, 3330-3335, Jun. 15, 1988.
Feng et al. Synthesis and Evaluation of Water-Soluble Paclitaxel Prodrugs. *Bioorganic & Medicinal Chemistry Letters* 12 (2002) 3301-3303.
Gao, Q., et al., "Drug-induced DNA repair: X-ray structure of a DNA-ditercalinium complex", *Proc. Natl. Acad. Sci. USA*, 88:2422-2426 (1991).
Gao, Q., et al., "Substitutions at C2' of daunosamine in the anticancer drug daunorubicin alter its DNA binding sequence specificity", *Eur. J. Biochem.*, 240:331-335 (1996).
Garbesi, A., et al., "Synthesis and binding properties of conjugates between oliogodeoxynucleotides and daunorubicin derivatives," *Nucleic Acids Research*, 25(11):2121-2128 (1997).
Hashida, M. et al., "Targeted delivery of plasmid DNA complexed with galactosylated poly(L-lysine)," *Journal of Controlled Release*, 53:301-310 (1998).
Hermanson G. Bioconjugate Techniques pp. 548-569 (1996).
Herschlag, D., et al., "An RNA Chaperone Activity of Non-Specific RNA Binding Proteins in Hammerhead Ribozyme Catalysis," *The EMBO Journal*, 13(12):2913-2924 (1994).
Hill, G.C., et al., "Computer Simulation of the Binding of Naphthyridinomycin and Cyanocycline A to DNA", *J. Med. Chem.*, 34:2079-2088 (1991).
Hook, R.J., et al., "Synthesis of polyamine-linked bis-daunomycin hydrazones and their interaction with DNA", *Anti-Cancer Drug Design*, 4:173-189 (1989).
Hope, M.J., et al., "Cationic lipids, phosphatidylethanolamine and intracellular delivery of polymeric, nucleic acid-based drugs (Review)", *Molecular Membrane Biology*, 15:1-14 (1998).
Huff, A.C. and Kreuzer, K.N., "Evidence for a Common Mechanism of Action for Antitumor and Antibacterial Agents That Inhibit Type II DNA Topoisomerases," *The Journal of Biological Chemistry*, 265(33):20496-20505 (1990).
Jaschke, A. et al., "Synthesis and Properties of Oligodeoxyribonucleotide-Polyethylene Glycol Conjugates," *Nucleic Acids Res.*, 22(22):4810-4817 (1994).
Jolles, B., et al., "Comparison of DNA sequence selectivity of anthracycline antibiotics and their 3'-hydroxylated analogs", *Chemico-Biological Interactions*, 100:165-176 (1996).
Jordan, Craig V. Tamoxifen: A Most Unlikely Pioneering Medicine. *Nature Reviews*. vol. 2, Mar. 2003, 205-213.

Kawaguchi, T. et al., "Stability, Specific Binding Activity, and Plasma Concentration in Mice of and Oligodeoxynucleotide Modified at 5'—Terminal with Poly(ethylene glycol)", *Biol. Pharm. Bull.*, 18(3):474-476 (1995).

Katayose, S. et al., "Water-Soluble Polyion Complex Associates of DNA and Poly(ethylene glycol)-Poly(L-lysine) Block Copolymer," *Bioconjugate Chem.*, 8(5):702-707 (1997).

Krugh, T.R., "Drug-DNA interactions", *Current Opinion in Structural Biology*, 4:351-364 (1994).

Kumar, S. et al., "Solution structure of a highly stable DNA duplex conjugated to a minor groove binder", *Nucleic Acid Research*, 26(3):831-838 (1998).

Lipscomb, L.A., et al., "Water Ring Structure at DNA Interfaces: Hydration and Dynamics of DNA-Anthracycline Complexes," *Biochemistry*, 33:3649-3659 (1994).

Matysiak, S., et al., "Acetal Oligonucleotide Conjugates in Antisense Strategy," *Nucleosides & Nucleotides*, 16 (5&6), 855-861 (1997).

McConnaughie, A.W. and Jenkins, T.C., "Novel Acridine-Triazenes as Prototype Combilexins: Synthesis, DNA Building, and Biological Activity", *J. Med. Chem.*, 38:3488-3501 (1995).

Mee, S.L., et al., "S16020-2, a new Highly Cytotoxic Antitumor Olivacine Derivative: DNA Interaction and DNA Toposiomerase II Inhibition," *Molecular Pharmacology*, 53:213-220 (1998).

Morham, S.G. and Suman, S., "Covalent and noncovalent DNA Binding by Mutants of Vaccinia DNA Topoisomerase I*", *J. Biol. Chem.*, 267(22):15984-15992 (1992).

Oxenius, A. et al., "CpG-Containing Oligonucleotides Are Efficient Adjuvants for Induction of Protective Antiviral Immune Reponses with T-Cell Peptide Vaccines", *J. Virol.* 73(5):4120-4126 (1999).

Papisov M.I. et al. "Semisynthetic Hydrophilic Polyals" *Biomacromolecules* 2005, vol. 6, pp. 2659-2670.

Papisov, M et al. Fully biodegradable hydrophilic polyals (polyacetals and polyketals). 29th Int. Symp. on Controlled Release of Bioactive Materials, 2002, Seoul, Korea. Controlled Release Society, Deerfield, IL, 2002; paper # 465.

Papisov, M. (1998) Theoretical considerations of RES-avoiding liposomes. Adv. Drug Delivery Rev., 32, 119-138.

Papisov, M. (2001) Acyclic polyacetals from polysaccharides. (Biopolymers from polysaccharides and agroproteins), ACS Symposium Series 786, pp. 301-314.

Papisov, M. et al (1996) A long-circulating polymer with hydrolizable main chain. 23-rd International Symposium on Controlled Release of Bioactive Materials, Kyoto, Japan, 1996; Controlled Release Society, Deerfield, IL,; 107-108.

Papisov, M. et al. Fully biodegradable hydrophilic polyacetals for macromolecular radiopharmaceuticals. 49-th Annual Meeting of The Society of Nuclear Medicine, Los Angeles, CA, 2002. J. Nuc. Med. 2002, 43:5 (abstract) p. 377P.

Papisov, M. et al. Hydrophilic Polyals: Biomimetic Biodegradable Stealth Materials for Pharmacology and Bioengineering. Proceedings of 226th Natl. Meeting of American Chemical Society, New York, NY, 2003.

Papisov, MI et al. (1998) Model cooperative (multivalent) vectors for drug targeting. 25th Int. Symp. on Controlled Release of Bioactive Materials, 1998, Las Vegas, Nevada, USA; Controlled Release Society, Deerfield, IL,170-171.

Papisov, MI. Modeling in vivo transfer of long-circulating polymers (two classes of long circulating polymers and factors affecting their transfer in vivo). Adv. Drug Delivery Rev., Special issue on long circulating drugs and drug carriers, 1995, 16:127-139.

Patel, D.J., et al., "Hydrogen bonding, overlap geometry and sequence specificity in anthracycline antitumor antibiotic: DNA complexes in solution", *Proc. Natl. Acad. Sci*, USA, 78(6):3333-3337 (1981).

Pearlman, L.F. and Simpkins, H., "The Differential Effects produced by Daunomycin and Adriamycin on RNA, Polynucleotides, Singe Stranded, Supercoiled DNA, and Nucleosomes", *Biochemical and Biophysical Research Communications*, 131 (2): 1033-1040 (1985).

Phillips, D.R., DNA sequence-specific adducts of adriamycin and mitomycin C, *FEBS*, 246(1)(2):233-240 (1989).

Phillips, D.R., "Kinetics and Sequence Specificity of Drug-DNA Interactions: An in Vitro Transcription Assay", *Biochemistry*, 25:7355-7362 (1986).

Pullman, B., Sequence specificity in the binding of anti-tumor anthracyclines to DNA: a success of theory, *Anti-Cancer Drug Design*, 7:95-105 (1991).

Rajur, S.B., et al., "Covalent Protein-Oligonucleotide Conjugates for Efficient Delivery of Antisense Molecules", *Bioconjugate Chem.*, 8:935-940 (1997).

Rizzo, V., et al., "Association of Anthracyclines and Synthetic Hexanucleotdies, Structural Factors Influencing Sequence Specificity", *J. Molec. Recognition*, 2(3):132-141 (1989).

Searle, M.S., "NMR Studies of Drug-DNA Interactions", *Progress in NMR Spectroscopy*, 25:403-480 (1993).

Skorobogaty, A., et al., "Elucidation of the DNA Sequence Preference of Daunomycin", *Drug Design and Delivery*, 3:125-151 (1988).

Sriram, M., et al., "Molecular Structure of Antitumor Drug Steffimycin and Modelling of its Binding to DNA", *J. Biomolecular Structure & Dynamics*, 9(2):251-269 (1991).

Taatjes, D.J., et al., Epidoxoform: A Hydrolytically More Stable Anthracycline-Formaldehyde Conjugate Toxic to Resistant Tumor Cells, *J. Med. Chem.*, 41:1306-1314 (1998).

Tomlinson, et al., "Poly-acetal-Doxorubicin Conjugates Designed for pH-Dependent Degradation," *Bioconjugate Chem.* 2003, 14, 1096-1106.

Trist, H. and Phillips, D.R., "In vitro transcription analysis of the role of flanking sequence on the DNA sequence specificity of Adriamycin", *Nucleic Acids Research*, 17(10):3673-3688 (1989).

van Houte, L.P.A., et al., "The Antitumor Drug Nogalamycin Forms Two Different Intercalation complexes with d(GCGT)-d(ACGC)", *Biochemistry*, 32:1667-1674 (1993).

Vedaldi, D., et al., "Sequence Specificity in DNA for the Interaction with Adriamycin or Daunomycin", *Il Farmaco—Ed. Sc.*, 9:571-581 (1982).

Veronese F.M. and M. Morpurgo, Bioconjugation in pharmaceutical chemistry, *Il Farmaco* 54:497-516 (1999).

Wang, J. et al., "Use of a Polyethylene Glycol-Peptide Conjugate in a Competition Gel Shift Assay for Screening Potential Antagonists of HIV-1 Tat Protein Binding to TAR RNA," *Anal. Biochem.* 232:238-242 (1995).

Wang L., et al., "Inhibition of Topoisomerase I Function by Nitidine and Fagaronine", *Chem. Res. Toxicol.*, 6:813-818 (1993).

Yang, X.-L. and Wang, A. H.-J., "Structural Studies of Aton-Specific Anticancer Drugs Acting on DNA," *Pharmacology & Therapeutics* 83:181-215 (1999).

Yurkovetskiy, A. et al. Biodegradable polyal carriers for protein modification. 29th Int. Symp. on Controlled Release of Bioactive Materials, 2002, Seoul, Korea. Controlled Release Society, Deerfield, IL, 2002; paper # 357.

Yurkovetskiy, A. et al. Biodegradable polyals for protein modification. Controlled Release Society's Winter Symposium, Salt Lake City, Utah, 2003.

Yurkovetsky, A. et al., Fully Degradable Hydrophilic Polyals for Protein Modification. Biomacromolecules 2005, 6, 2648-2658.

Zangemeister-Wittke, U. et al., "Synergistic cytotoxicity of bcl-2 antisense oligodeoxynucleotides and etoposide, doxorubicin and cisplatin on small-cell lung cancer cell lines," *British Journal of Cancer*, 78(8):1035-1042 (1998).

Zalipsky et al. Attachment of Drugs to Polyethylene Glycols. *Eur. Polym. J.* vol. 19, No. 12, pp. 1177-1183, 1983.

Ziegler, A., et al., "Induction of Apoptosis in Small-Cell Lung Cancer Cells by an Antisense Oligodeoxynucleotide Targeting the Bcl-2 Coding Sequence," *Journal of the National Cancer Institute*, 89(14):1027-1036 (1997).

US 5,484,894, 01/1996, Woiszwillo (withdrawn)
US 5,849,884, 12/1998, Woiszwillo (withdrawn)

* cited by examiner

SEQUENCE LISTING

```
<160> NUMBER OF SEQ ID NOS: 1

<210> SEQ ID NO 1
<211> LENGTH: 146
<212> TYPE: PRT
<213> ORGANISM: Homo sapiens

<400> SEQUENCE: 1

Val Pro Ile Gln Lys Val Gln Asp Asp Thr Lys Thr Leu Ile Lys Thr
1               5                   10                  15
```

-continued

```
Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
            85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
            130                 135                 140

Gly Cys
145
```

PROTEIN CONJUGATES WITH A WATER-SOLUBLE BIOCOMPATIBLE, BIODEGRADABLE POLYMER

This application is a Continuation-in-part of and claims priority under 35 U.S.C. §120 to U.S. application Ser. No. 10/622,998, filed Jul. 18, 2003, now U.S. Pat. No. 7,160,924, issued on Jan. 9, 2007, which claims priority under 35 U.S.C. §119(e) to U.S. Provisional Application No. 60/397,509, filed Jul. 19, 2002, the contents of which are hereby incorporated by reference in their entirety. This application is also a continuation-in-part of and claims priority under 35 U.S.C. §120 to co-pending U.S. patent application Ser. No. 10/994,213, filed on Nov. 19, 2004, which is a continuation of U.S. application Ser. No. 09/634,320, filed on Aug. 9, 2000, now U.S. Pat. No. 6,822,086, issued on Nov. 13, 2004, which claims priority under 35 U.S.C. §119(e) to U.S. Provisional Application No. 60/147,919, filed Aug. 9, 1999, the contents of which are hereby incorporated by reference.

BACKGROUND OF THE INVENTION

Due to recent advances in genetic and cell engineering technologies, proteins known to exhibit various pharmacological actions in vivo are capable of production in large amounts for pharmaceutical applications. Examples of such proteins include erythropoietin (EPO), granulocyte colony-stimulating factor (G-CSF), interferons (alpha, beta, gamma, consensus), tumor necrosis factor binding protein (TNFbp), interleukin-1 receptor antagonist (IL-1ra), brain-derived neurotrophic factor (BDNF), kerantinocyte growth factor (KGF), stem cell factor (SCF), megakaryocyte growth differentiation factor (MGDF), osteoprotegerin (OPG), interferon (IFN), consensus interferon (CIFN), novel erythropoiesis stimulating protein (NESP), glial cell line derived neurotrophic factor (GDNF) soluble extracellular domain of tumor necrosis factor receptor fused to the Fc domain of an antibody (etanercept), antibodies to specific to various different antigens, and obesity protein (OB protein). OB protein may also be referred to herein as leptin.

The availability of such recombinant proteins has engendered advances in protein formulation and chemical modification. One goal of chemical modification is protein protection. Chemical attachment may effectively block a proteolytic enzyme from physical contact with the protein backbone itself, and thus prevent degradation. Additional advantages include, under certain circumstances, increasing the stability and circulation time of the therapeutic protein, thereby increasing its therapeutic efficacy by reducing the ability of the immune system to detect and eliminate the therapeutic moiety.

There are several methods of chemical modification of useful therapeutic proteins which have been reported. For example, chemical modification using water soluble polymers (including, but not limited to, polyethylene glycols, copolymers of ethylene glycol/propylene glycol, polyvinyl alcohol, carboxymethylcellulose, polyvinyl pyrrolidone, poly-1,3-dioxolane, poly-1,3,6-trioxane, ethylene/maleic anhydride copolymer, polyaminoacids (either homopolymers or random copolymers), and dextran) has been extensively studied, and several polymer-protein conjugate formulations having improved pharmacological properties, e.g., enhanced serum half-life, improved stability and solubility, and decreased immunogenicity have been reported.

U.S. Pat. No. 5,824,784, discloses N-terminally monopegylated granulocyte colony stimulating factor ("G-CSF") and N-terminally monopegylated consensus interferon ("N-terminally monopegylated" denoting that the protein moiety has attached to it a single polyethylene glycol moiety at the N-terminus) which demonstrate, inter alia, increased serum half-life and improved stability. Chemical modification with a single 20 kDa polyethylene glycol (PEG) polymer at the N-terminus of leptin results in a highly efficacious molecule which demonstrates substantial dose reduction and increased solubility relative to the unmodified native protein; see, e.g., PCT WO 96/40912.

Unfortunately, there are still a few limitations associated with certain such chemical modifications. For example, the use of polymers in chronic applications and/or in relatively large amounts, the potentially undesirable effects of the accumulation of high molecular weight, synthetic, non-biodegradable polymers are of concern. In addition, PEG-protein conjugates have been found to accumulate in kidney vacuoles when administered regularly over a period of time at high doses; see e.g., Conover et al., *Artificial Organs*, 21(5):369-378 (1997); Bendele et al., *Toxicological Sciences*, 42:152 (1997). Although it is not known if such vacuoles are detrimental to the health of an individual, it is preferable that drug administration have no associated abnormalities.

There would thus be a clear advantage for a biodegradable, biocompatible, water soluble polymeric carrier of proteins wherein the polymeric carrier can be metabolized or hydrolyzed and eventually eliminated from the body. The present invention addresses this issue and provides methods for preparing protein conjugates with a water-soluble biodegradable, biocompatible polyacetal polymer. Importantly, the polyacetal-protein conjugates described herein were biologically active and did not produce any undesirable side effects (e.g., kidney vacuole formation) in experimental animals.

SUMMARY OF THE INVENTION

The present invention relates to biodegradable, biocompatible polyacetal derivatives, and methods for making and using them. Importantly, the polyacetal derivatives can be conjugated to proteins to provide for polyacetal-protein conjugates which demonstrate advantages in bioavailability and biocompatibility compared to unconjugated proteins, without any undesirable side effects.

The present invention further relates to processes for preparing the polyacetal-protein conjugates described above. The principal embodiment of the method for making the preparation of the polyacetal-protein conjugate comprises: (a) preparing a poly-acetal derivative; (b) conjugating said polyacetal derivative to a protein to provide a polyacetal-protein conjugate; (c) isolating said polyacetal-protein conjugate. In a more specific embodiment the polyacetal is poly-(hydroxymethylene hydroxymethylformal). In another specific embodiment, the poly-(hydroxymethylene hydroxymethylformal)-protein conjugate is substantially homogenous.

The present invention further relates to all of the polyacetal-protein conjugates as above, in a pharmaceutically acceptable carrier.

The present invention also relates to methods of treatment of individuals using the polyacetal-protein conjugates as above.

DETAILED DESCRIPTION OF THE INVENTION

The present invention relates to preparations of chemically modified proteins, and methods of making or using them. In a particular embodiment, the invention relates to substantially homogenous preparations of chemically modified proteins. More specifically, the invention teaches preparations of proteins conjugated to polyacetals.

U.S. Pat. Nos. 5,811,510, 5,863,990, and 5,958,398 describe biodegradable, biocompatible polyacetals, methods for their preparation, and methods for treating and studying mammals by administration of biodegradable, biocompatible polyacetals. The biodegradable, biocompatible polyacetals are described as distinct from naturally-occurring polysaccharides, in that the polysaccharide ring structure is cleaved during the synthesis of the biodegradable, biocompatible polyacetals and is essentially absent from the polymer structure.

Further, the biodegradable, biocompatible polyacetals are said to have a higher degree of biocompatibility relative to the polysaccharides from which they are derived, since they generally do not contain cyclic carbohydrates—which are potentially receptor recognizable. One suitable polyacetal polymer included in the disclosures is poly-(hydroxymethylene hydroxymethylformal).

However, U.S. Pat. Nos. 5,811,510, 5,863,990, and 5,958,398 do not teach conjugating biodegradable, biocompatible polyacetals to proteins as used herein, with the expectation of improving bioavailability, bioactivity and reducing or eliminating kidney vacuole formation upon injection of these conjugates in patients.

As described herein, the conjugation of proteins to biodegradable, biocompatible polyacetals can occur by using a variety of functional derivatives of biodegradable, biocompatible polyacetals which react with functional groups available on the proteins for their modification. Such reactions can result in the conjugation of the protein to a polyacetal amide, amino, urethane, imino, ester, thioether or any other chemical linkage known in the art.

As used herein, the term "chemically modified protein" of the invention is understood to be a biodegradable, biocompatible polyacetal, e.g., a poly-(hydroxymethylene hydroxymethylformal), conjugated protein of the invention, wherein the biodegradable, biocompatible polyacetal has been derivatized such that it has a functional side group capable of reacting with a corresponding functional group on a protein.

The term "protein", as used herein, is understood to include peptides, polypeptides, consensus molecules, fusion proteins, purified naturally occurring proteins, artificially synthesized proteins, analogs, derivatives or combinations thereof.

"Substantially homogenous" as used herein means that the only chemically modified proteins observed are those having one biodegradable, biocompatible polyacetal "modifier" (e.g., poly-(hydroxymethylene hydroxymethylformal)) moiety. The preparation may contain unreacted (i.e., lacking a modifier moiety) protein. As ascertained by peptide mapping and N-terminal sequencing, one example below provides for a preparation which is at least 90% chemically modified protein, and at most 10% unmodified protein. Preferably, the chemically modified material is at least 95% of the preparation and most preferably, the chemically modified material is 99% of the preparation or more.

The chemically modified material has biological activity. The present substantially homogenous biodegradable, biocompatible polyacetal-protein preparations provided herein are those which are homogenous enough to display the advantages of a homogenous preparation, e.g., ease in clinical application in predictability of lot to lot pharmacokinetics.

As used herein, biologically active agents refers to proteins, whether human or animal, useful for prophylactic, therapeutic or diagnostic application. These proteins have activity such as specific binding to a receptor, ligand or epitope. The biological activity is not enzymatic.

The biologically active protein can be natural, synthetic, semi-synthetic or a derivative thereof. A wide range of biologically active agents are contemplated. These include but are not limited to antibodies, fusion proteins, peptides, peptibodies, hormones, cytokines, hematopoietic factors, growth factors, antiobesity factors, trophic factors, and anti-inflammatory factors (see also U.S. Pat. No. 4,695,463 for additional examples of useful biologically active agents). One skilled in the art will readily be able to adapt a desired biologically active agent to the compositions of present invention.

Such proteins would include but are not limited to interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582,823, and PCT Publication No. 94/17185, hereby incorporated by reference including drawings), stem cell factor (PCT Publication Nos. 91/05795, 92/17505 and 95/17206, hereby incorporated by reference including drawings), osteoprotegerin (PCT Publication No. 97/23614, hereby incorporated by reference including drawings) and leptin (OB protein).

The type of leptin used for the present polyacetal-leptin (namely, poly-(hydroxymethylene hydroxymethylformal)-leptin) preparations may be selected from those described in PCT International Publication Number WO 96/05309, as cited above and herein incorporated by reference in its entirety. FIG. 3 of that publication depicts the full deduced amino acid sequence derived for human leptin (referred to as the human "OB" protein). The amino acids are numbered from 1 to 167. A signal sequence cleavage site is located after amino acid 21 (Ala) so that the mature protein extends from amino acid 22 (Val) to amino acid 167 (Cys). For the present disclosure, a different numbering is used herein, where the amino acid position 1 is the valine residue which is at the beginning of the mature protein. The amino acid sequence for mature, recombinant methionyl human leptin is presented herein as SEQ ID NO: 1, where the first amino acid of the mature protein is valine (at position 1) and a methionyl residue is located at position −1 (not included in the sequence below).

```
                                            SEQ ID NO: 1
         V P I Q K V Q D D T K T L I K T I V

.T R I N D I S H T Q S V S S K Q K V T G

.L D F I P G L H P I L T L S K M D Q T L

.A V Y Q Q I L T S M P S R N V I Q I S N

.D L E N L R D L L H V L A F S K S C H L

P W A S G L E T L D S L G G V L E A S G

.Y S T E V V A L S R L Q G S L Q D M L W

Q L D L S P G C
```

However, as with any of the present leptin moieties, the methionyl residue at position −1 may be absent.

Alternatively, one may use a natural variant of human leptin, which has 145 amino acids and, as compared to rmetHu-leptin of SEQ ID NO: 1, has a glutamine absent at position 28.

Generally, the leptin moiety for human pharmaceutical use herein will be capable of therapeutic use in humans (see also, animal leptins, below). Thus, one may empirically test activity to determine which leptin moieties may be used. As set forth in WO 96/05309, leptin protein in its native form, or fragments (such as enzyme cleavage products) or other truncated forms and analogs may all retain biological activity. Any of such forms may be used as a leptin moiety for the present the polyacetal-leptin conjugates, although such altered forms should be tested to determine desired characteristics. See also, PCT International Publication Numbers WO 96/40912, WO 97/06816, 97/18833, WO 97/38014, WO 98/08512 and WO 98/28427, herein incorporated by reference in their entireties.

One may prepare an analog of recombinant human leptin by altering amino acid residues in the recombinant human sequence, such as substituting the amino acids which diverge from the murine sequence. Murine leptin is substantially homologous to human leptin, particularly as a mature protein and, further, particularly at the N-terminus. Because the recombinant human protein has biological activity in mice, such an analog would likely be active in humans. For example, in the amino acid sequence of native human leptin as presented in SEQ ID NO: 1, one may substitute with another amino acid one or more of the amino acids at positions 32, 35, 50, 64, 68, 71, 74, 77, 89, 97, 100, 101, 105, 106, 107, 108, 111, 118, 136, 138, 142 and 145. One may select the amino acid at the corresponding position of the murine protein (see Zhang et al., 1994, supra) or another amino acid.

One may further prepare "consensus" molecules based on the rat OB protein sequence. Murakami et al., *Biochem. Biophys. Res. Comm.*, 209:944-52 (1995) herein incorporated by reference. Rat OB protein differs from human OB protein at the following positions (using the numbering of SEQ ID NO: 1): 4, 32, 33, 35, 50, 68, 71, 74, 77, 78, 89, 97, 100, 101, 102, 105, 106, 107, 108, 111, 118, 136, 138 and 145. One may substitute with another amino acid one or more of the amino acids at these divergent positions. The positions underlined are those in which the murine OB protein as well as the rat OB protein are divergent from the human OB protein and, thus, are particularly suitable for alteration. At one or more of the positions, one may substitute an amino acid from the corresponding rat OB protein, or another amino acid.

Other analogs may be prepared by deleting a part of the protein amino acid sequence. For example, the mature protein lacks a leader sequence (−22 to −1). One may prepare the following truncated forms of human OB protein molecules (using the numbering of SEQ ID NO: 1):

(i) amino acids 98-146;
(ii) amino acids 1-99 and (connected to) 112-146;
(iii) amino acids 1-99 and (connected to) 112-146 having one or more of amino acids 100-111 sequentially placed between amino acids 99 and 112.

In addition, the truncated forms may also have altered one or more of the amino acids which are divergent (in the murine, rat or rhesus OB protein) from human OB protein. Furthermore, any alterations may be in the form of altered amino acids, such as peptidomimetics or D-amino acids.

Also included are those proteins as set forth above with amino acid substitutions which are "conservative" according to acidity, charge, hydrophobicity, polarity, size or any other characteristic known to those skilled in the art. These are set forth in Table 1, below. See generally, Creighton, *Proteins, passim* (W.H. Freeman and Company, N.Y., 1984); Ford et al., *Protein Expression and Purification* 2:95-107 (1991), which are herein incorporated by reference.

TABLE 1

| Conservative Amino Acid Substitutions | |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |
| Small: | glycine |
|  | alanine |
|  | serine |
|  | threonine |
|  | methionine |

Interleukin-1 receptor antagonist (IL-1ra) is a human protein that acts as a natural inhibitor of interleukin-1. Preferred receptor antagonists, as well as methods of making and using thereof, are described in U.S. Pat. No. 5,075,222 (referred to herein as the '222 patent); WO 91/08285; WO 91/17184; AU 9173636; WO 92/16221; WO93/21946; WO 94/06457; WO 94/21275; FR 2706772; WO 94/21235; DE 4219626, WO 94/20517; and WO 96/22793, the disclosures of which are incorporated herein by reference. The proteins include glycosylated as well as non-glycosylated IL-1 receptor antagonists.

Specifically, three useful forms of IL-1ra and variants thereof are disclosed and described in the '222 patent. The first of these, IL-1raα, is characterized as a 22-23 kD molecule on SDS-PAGE with an approximate isoelectric point of 4.8, eluting from a Mono Q FPLC column at around 52 mM NaCl in Tris buffer, pH 7.6. The second, IL-1raβ, is characterized as a 22-23 kD protein, eluting from a Mono Q column at 48 mM NaCl. Both IL-1raα and IL-1raβ are glycosylated. The third, IL-1raα, is characterized as a 20 kD protein, eluting from a Mono Q column at 48 mM NaCl, and is non-glycosylated. All three of these inhibitors possess similar functional and immunological activities.

IL-1ra was produced in *E. coli* using methods such as those described in e.g., U.S. Pat. No. 5,075,222. One disclosed method consists of isolating the IL-1ra from human monocytes, where they are naturally produced. A second disclosed method involves isolating the gene responsible for coding IL-1ra, cloning the gene in suitable vectors and cells types, expressing the gene to produce the inhibitors and harvesting the inhibitors. The latter method, which is exemplary of recombinant DNA methods in general, is a preferred method. Recombinant DNA methods are preferred in part because they are capable of achieving comparatively greater amounts of protein at greater purity. Thus, the invention also encompasses IL-1ra containing an N-terminal methionyl group as a consequence of expression in prokaryotic cells, such as *E. coli*.

In addition, biologically active agents can also include but are not limited to antibodies of any isotype. Specific examples include commercially available antibodies such as muromonab-CD3 (Orthoclone OKT-3™, Ortho Biotech), abciximab (ReoPro™, Lilly), rituximab (Rituxan™, IDEC), dacliximab (Zenapak™, Roche Laboratories), basiliximab (Simulect™, Novartis), infliximab (Remicade™, Centocor), palivizumab (Synagis™, MedImmune), trastuzumab (Herceptin™, Genentech), gemtuzuman ozogamicin (Mylotarg™, Wyeth), and alemtuzumab (Campath™, Berlex). Further Examples of antibodies or antibody/cytotoxin or antibody/luminophore conjugates contemplated for conjugation to the polymers of the invention include those antibodies that recognize one or more of the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-4, IL-5, IL-8, IL-10, IL-2 receptor, IL-4 receptor, IL-6 receptor, IL-13 receptor, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or polypeptides expressed on breast, colon, squamous cell, prostate, pancreatic, lung, and/or kidney cancer cells and/or on melanoma, glioma, or neuroblastoma cells, TRAIL receptors 1, 2, 3 and 4, the necrotic core of a tumor, integrin alpha 4 beta 7, the integrin VLA-4, B2 integrins, TNF-a, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-?-1 receptor, HLA-DR 10 beta, HLA-DR antigen, L-selectin, IFN-?, Respiratory Syncitial Virus, human immunodeficiency virus (HIV), hepatitis B virus (HBV), *Streptococcus mutans*, and *Staphylococcus aureus*.

Additional biologically active agents include fusion proteins such as the soluble extracellular domain of the tumor necrosis factor receptor (TNFR) fused to the Fc domain of an immunoglobulin (etanercept), insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase, kallikrein, flt3 ligand, CD40 ligand, thrombopoietin, calcitonin, Fas ligand, ligand for receptor activator of NF-kappa B (RANKL), tumor necrosis factor (TNF)-related apoptosis-inducing ligand (TRAIL), thymic stroma-derived lymphopoietin, mast cell growth factor, stem cell growth factor, epidermal growth factor, RANTES, growth hormone, insulinotropin, parathyroid hormone, glucagon, interleukins 1 through 18, colony stimulating factors, lymphotoxin-beta, leukemia inhibitory factor, oncostatin-M, Eph or Ephrin molecules that include the various ligands for cell surface molecules ELK and Hek (such as the ligands for eph-related kinases, also known as the LERKS).

The water-soluble, biocompatible polymers contemplated for use are those described in U.S. Pat. Nos. 5,811,510, 5,863, 990, and 5,958,398 and the methods of making said polymers are incorporated herein by reference. The biodegradable, biocompatible polyacetals are described as distinct from naturally-occurring polysaccharides, in that the polysaccharide ring structure is cleaved during the synthesis of the biodegradable, biocompatible polyacetals and is essentially absent from the polymer structure. Further, the biodegradable, biocompatible polyacetals are said to have a higher degree of biocompatibility relative to the polysaccharides from which they are derived, since they generally do not contain cyclic carbohydrates-which are potentially receptor recognizable. A preferred biodegradable, biocompatible polyacetal polymer contemplated for use herein is poly-(hydroxymethylene hydroxymethylformal), or PHF.

Polymers of this invention are used in an activated form, i.e., polymer molecules comprise functional groups suitable for conjugation with a protein. Such groups can be introduced using any strategy known in the art, for example, via a chemical reaction between the polymer and a bifunctional reagent comprising said functional group, or its precursor, and a second functional group suitable for conjugation with the polymer.

The preferred protein-binding functional groups of this invention include groups capable of binding functional groups present in the protein structure. Since protein binding through amino groups and thiol groups in aqueous media is often preferable, the preferred protein binding functional groups of this invention are groups capable of binding either amino groups or mercapto groups in aqueous media or in polar solvents, or mixtures thereof. Such groups are generally known in organic and bioconjugate chemistry. Examples of such groups are maleimido groups, pyridyldithio groups, and N-hydroxysuccinimide ester groups.

The preferred second functional group of this invention is a carboxyl group, which is, preferably, activated either in situ or in advance. Activation is performed via formation of a carboxyl group derivative suitable for condensation with functional groups present in the polymer structure, such as, primary or secondary hydroxyls. Such derivatives are formed using reagents and methods generally known in organic and bioconjugate chemistry. The preferred derivatives are esters and O-acylisoureas, including, but not limited to, nitrophenyl ester, N-hydroxysuccinimide ester, tetrafluorophenyl ester; N,N'-dicyclohexyl-O-acylisourea, N,N'-diisopropyl-O- acylisourea, N-(3-dimethylaminopropyl)-N'-ethyl-O-acylisourea, 1-cyclohexyl-3-(2-morpholinoethyl)-O-acylisourea.

Preparation of an Activated Polymer with Said bifunctional reagent is preferably performed in a suitable non-aqueous media, i.e., a solvent or a solvent mixture in which the polymer and all reagents are sufficiently soluble, and where none of the component adversely interferes with any of the reagents or with any processes constituting the reaction of conjugation. Examples of such media include, but are not limited to, pyridine (Py), dimethylformamide (DMF), dimethylsulfoxide (DMS), methanol, and mixtures thereof. The polymer, the bifunctional reagent, and, where necessary, one or more coupling reagents and catalysts, are combined in such media and allowed to react for a sufficient amount of time. The process can be further optimized by adjustments in the reagent concentration and composition, acidity, temperature, and other parameters. The reaction media is preferably isolated from ambient air, in particular to avoid interactions of any reagent with oxygen or water. To achieve such isolation, the reaction can be conducted in a vessel filled with dry argon or nitrogen.

In one of the preferred embodiments, the bifunctional reagent is a cyclic anhydride of a dicarbonyl acid, for example, succinic anhydride. The reaction of succinic anhydride, with PHF, preferably under argon and in the presence of a catalyst, results in the succinilated PHF, i.e., a polymer comprising succinic acid bound to the polymer via one of the carboxyls, while another carboxyl remains available for further modification. The latter carboxyl can be further activated to form an active ester or an O-acylisourea; the resultant activated polymer can be further purified, isolated, and reacted with a protein to form a conjugate. Alternatively, the succinilated polymer can be purified and reacted with a protein in the presence of a suitable coupling reagent, such as a carbodiimide. The carboxyl group and its activated derivatives is generally known to bind proteins through amino groups of lysine, terminal amino groups, and, at least in some instances, through histidine, tyrosine, and other amino acids.

In another preferred embodiment, the bifunctional reagent is a maleimidocarboxylic acid, for example, maleimidopropionic acid, or an activated derivative thereof, for example, an activated ester, an anhydride, a halogenanhydride, or an O-acylisourea. The reaction of maleimidocarboxylic acid with PHF, preferably under argon and in the presence of a catalyst, results in the polymer comprising maleimide groups suitable for conjugation with proteins. Such polymers is further purified, isolated, and reacted with a protein to form a conjugate. The maleimido group is generally known to bind proteins through mercaptogroups of cysteine.

Alternatively, a functional group suitable for conjugation with proteins can be introduced into the polymer structure during polymer synthesis. For example, lateral cleavage of Dextran B-512 can be performed at periodate:glucose monomer ratio of less than 2:1 mol/mol, preferably between 1.95:1 to 1.5:1, which results in ring opening without complete cleavage of carbon 3 in some carbohydrate units. Borohydride reduction results in vicinol glycol formation in such units, which can be confirmed by proton NMR and reaction with periodate.

Proteins modified using one of the above approaches can be further fractionated and purified to obtain a conjugate preparation with a desired size distribution, protein content, charge, or other parameter.

The biological properties of protein conjugates are generally known to depend on several parameters. Although it is not bound by theory, in some particular instances, the size (molecular weight) and size distribution of polymer molecules may be of particular importance. Although it is conceivable that this invention can use polymers within molecular weights as low as 1 kDa or lower, or as high as 500 kDa or higher, the preferred molecular weight range of this invention is 5 kDa to 300 kDa, most preferable 20 kDa to 150 kDa.

The invention also contemplates pharmaceutical compositions comprising effective amounts of a selected biodegradable, biocompatible polyacetal conjugated protein, or derivative products, together with pharmaceutically acceptable diluents, preservatives, solubilizers, emulsifiers, adjuvants and/or carriers needed for administration. (See PCT 97/01331 hereby incorporated by reference.) The optimal pharmaceutical formulation for a desired biologically active agent will be determined by one skilled in the art depending upon the route of administration and desired dosage.

Exemplary pharmaceutical compositions are disclosed in Remington's Pharmaceutical Sciences (Mack Publishing Co., 18th Ed., Easton, Pa., pgs. 1435-1712 (1990)). The pharmaceutical compositions of the present invention may be administered by oral and non-oral preparations (e.g., intramuscular, subcutaneous, transdermal, visceral, IV (intravenous), IP (intraperitoneal), intraarticular, placement in the ear, ICV (intracerebralventricular), IP (intraperitoneal), intraarterial, intrathecal, intracapsular, intraorbital, injectable, pulmonary, nasal, rectal, and uterine-transmucosal preparations).

Therapeutic uses of the compositions of the present invention depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like interferons (see, U.S. Pat. Nos. 5,372,808, 5,541,293, hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,999,291, 5,581,476, 5,582,823, 4,810,643 and PCT Publication No. 94/17185, hereby incorporated by reference including drawings), stem cell factor (PCT Publication Nos. 91/05795, 92/17505 and 95/17206, hereby incorporated by reference including drawings), and the OB protein (see PCT publication Nos. 96/40912, 96/05309, 97/00128, 97/01010 and 97/06816 hereby incorporated by reference including figures). In addition, the present compositions may also be used for manufacture of one or more medicaments for treatment or amelioration of the conditions the biologically active agent is intended to treat.

One skilled in the art will be able to ascertain effective dosages by administration and observing the desired therapeutic effect. Preferably, the formulation of the conjugate will be such that between about 0.01 µg leptin moiety/kg body weight/day and 10 mg leptin moiety/kg body weight/day will yield the desired therapeutic effect. The effective dosages may be determined using diagnostic tools over time. For example, a diagnostic for measuring the amount of leptin in the blood (or plasma or serum) may first be used to determine endogenous levels of leptin protein. Such diagnostic tool may be in the form of an antibody assay, such as an antibody sandwich assay. The amount of endogenous leptin protein is quantified initially, and a baseline is determined. The therapeutic dosages are determined as the quantification of endogenous and exogenous leptin protein moiety (that is, protein, analog or derivative found within the body, either self-produced or administered) is continued over the course of therapy. The dosages may therefore vary over the course of therapy, with, for example, a relatively high dosage being used initially, until therapeutic benefit is seen, and lower dosages used to maintain the therapeutic benefits.

Therapeutic uses of polyacetal-leptin include weight modulation, the treatment or prevention of diabetes, blood lipid reduction (and treatment of related conditions), increasing lean body mass and increasing insulin sensitivity. Particular embodiments contemplate the use of poly-(hydroxymethylene hydroxymethylformal)-leptin conjugates.

Therapeutic uses of polyacetal-IL-1ra include those described in e.g., U.S. Pat. No. 5,075,222. Particular embodiments contemplate the use of poly-(hydroxymethylene hydroxymethylformal)-IL-1ra in the therapeutic uses contemplated above.

In addition, the present compositions may be used for manufacture of one or more medicaments for treatment or amelioration of the above conditions.

The following examples are offered to more fully illustrate the invention, but are not to be construed as limiting the scope thereof.

EXAMPLE 1

The water-soluble, biodegradable, biocompatible polymers, the 'polyacetals', contemplated for use in making conjugates of the present invention are those described in U.S. Pat. Nos. 5,811,510, 5,863,990, and 5,958,398. This example describes the synthesis of various biodegradable, biocompatible polyacetal derivatives, namely poly-(hydroxymethylene hydroxymethylformal) aldehyde and poly-(hydroxymethylene hydroxymethylformal) maleimide.

Synthesis of Fleximer1 (Maleimido-PHF1): PHF was prepared via exhaustive lateral cleavage of dextran B-512 by periodate oxidation. Dextran of Mn 20,000 Da (15 g) was dissolved in 30 mL of deionized water. Dextran solution was treated with 50 g of sodium metaperiodate dissolved in 1 L of deionized water on ice bath in a light protected reactor. The reaction mixture was incubated at 5° C. for 3 hours, and then at 25° C. for 10 hours. The reaction mixture was then filtered, desalted by flow dialysis, and treated with sodium borohydride (8 g) dissolved in 50 mL of deionized water at 0° C. After a 2 hour incubation, the pH was adjusted to 6.5 with 5 N HCl. The product was desalted and concentrated by flow dialysis using hollow fiber cartridge, cutoff 30 kDa. Then, the product was purified by gel chromatography on Sephadex G-25, using deionized water as an eluent. The polymer was recovered from the aqueous solutions by lyophilization; yield: 60%. Size exclusion chromatography showed the same elution profile as of the original dextran B-512; $^{13}$C and $^1$H NMR spectra were in agreement with the expected acyclic polyacetal structure.

Dry polymer, 10 g, and maleimidopropionic acid, 0.5 g, were dissolved in 100 ml pyridine. The reaction mixture was placed under argon. Then, 0.67 g of N,N'-dicyclohexyl carbodiimide and 0.1 g of dimethylaminopyridine were added, and the reaction mixture was incubated for 12 hours at 25° C., filtered and dried in vacuum. Then, the product was reconstituted in 100 ml cold deionized water and desalted on Sephadex G-25. Then 1 g NaCl were added to the polymer solution, and the solution was lyophilized.

Synthesis of Fleximer2: Synthesis was performed analogously, using dextran 512 with molecular weight of 180 kDa, and without NaCl addition at the last (lyophilization) step.

Synthesis of FleximerG20: PHF-glycol was prepared by controlled lateral cleavage of dextran B-512 at periodate:polymer molar ratio of 1.7:1, in order to obtain a polymer comprising vicinal diol groups. The polymer was prepared as described above for PHF. SEC analysis has shown no substantial difference between MW/MWD of the starting dextran B-512 and the resultant PHF-glycol. Vicinal glycol group content, as determined by consumption of periodate was 29±3% (mol/mol monomer). The polymer was lyophilized from deionized water.

Synthesis of FleximerG50: PHF-glycol with 25±2% glycol content was prepared as above, using dextran B-512 with molecular weight of 70 kDa. SEC analysis has shown no substantial difference between MW/MWD of the starting dextran B-512 and the resultant PHF-glycol. The polymer was lyophilized from deionized water.

EXAMPLE 2

This example describes the synthesis of various Fleximer1-leptin and Fleximer2-leptin conjugates. A recombinant methionyl human leptin analog, $^{78}$C-leptin, prepared as described in the Materials and Methods section below, was used for the conjugations.

Synthesis of Fleximer1-Leptin Conjugates

Preparation 1. 40.0 mg (2.48 µmol) of $^{78}$C-leptin (8.0 mL of a 5 mg/mL solution in 10 mM acetate pH 4) was diluted with 12 mL of maleimide buffer (20 mM phosphate pH 6.5 containing 5 mM EDTA) and the pH raised to 6.5 with NaOH. A solution of 40.0 mg (2.22 µmol) of Fleximer1 in 2.0 mL of maleimide buffer was added to the $^{78}$C-leptin solution and stirred in the cold room for 5 days.

The reaction mixture was then diluted with 23 mL of pH 3 water, the pH lowered to 3.5 with HCl and the mixture filtered through a 0.45 µm CA filter. The filtrate was loaded onto an SP16 FPLC column in 20 mM NaOAc pH 4 and eluted with a 0.5M NaCl gradient. Fractions 30-52 (184 mL) were combined, treated with 18.4 mL of 10× D-PBS and the pH raised to 7.0 with 1N NaOH. The combined fractions were placed in a 400 mL stirred cell with a YM-3 membrane, diluted to 350 mL with D-PBS and then concentrated to 35 mL (0.1471 mg/mL=5.1 mg protein), then further concentrated to 20 mL.

Preparation 2: 40.0 mg (2.48 µmol) of $^{78}$C-leptin (8.0 mL of a 5 mg/mL solution in 10 mM acetate pH 4) was diluted with 12 mL of maleimide buffer (20 mM phosphate pH 6.5 containing 5 mM EDTA) and the pH raised to 6.5 with NaOH. A solution of 200.0 mg (11.1 µmol) of Fleximer1 in 2.0 mL of maleimide buffer was added to the $^{78}$C-leptin solution and stirred in the cold room for overnight.

The reaction mixture was diluted with 23 mL of pH 3 water, the pH lowered to 3.5 with HCl and filtered through a 0.45 µm CA filter. The filtrate was loaded onto an SP16 FPLC column in 20 mM NaOAc pH 4 and eluted with a 0.5M NaCl gradient. Fractions 25-45 (0.0750 mg/mL=15.8 mg protein) were combined, treated with 21.0 mL of 10× D-PBS and the pH raised to 7.0 with 1N NaOH.

The products from Preparation 1 (20 mL) and Preparation 2 (210 mL) were combined and placed in a 200 mL stirred cell with a YM-3 membrane and concentrated to ~20 mL. This material was diluted with 150 mL of D-PBS and concentrated to near dryness. 5.0 mL of D-PBS were added to the cell to give 4.5 mL (4.07 mg/mL=18.3 mg protein) of product. This solution was diluted to 2.0 mg/mL with D-PBS, sterile filtered, vialed and submitted for in vivo testing.

Synthesis of Fleximer2-Leptin Conjugates 40.0 mg (2.48 µmol) of $^{78}$C-leptin (8.0 mL of a 5 mg/mL solution in 10 mM acetate pH 4) was diluted with 12 mL of maleimide buffer (20 mM phosphate pH 6.5 containing 5 mM EDTA) and the pH raised to 6.5 with NaOH. A solution of 137.5 mg (1.24 μmol) of Fleximer2 in 3.0 mL of maleimide buffer was added to the $^{78}$C-leptin solution and stirred in the cold room for 8 days.

The reaction mixture was diluted with 25 mL of D-PBS and filtered through a coarse sintered glass funnel. The filtrate was placed in a 200 mL Amicon stirred cell with a YM-100 membrane and diafiltered vs. D-PBS. A total of 485 mL of diafiltrate was collected. The retentate was concentrated to 10.7 mL (2.72 mg/mL=29.1 mg protein). This solution was diluted to 2.0 mg/mL with D-PBS, filtered (0.45 μm), vialed and submitted for in vivo testing.

EXAMPLE 3

The in vivo efficacy of the Fleximer1-leptin conjugate and Fleximer2-leptin conjugate was tested in wild-type mice by monitoring weight loss relative to a buffer control. The Fleximer1-leptin preparation was tested vs. a 20 kDa monoPEG-leptin preparation and each preparation was administered at 1 mg/kg/single dose, 10 mg/kg/single dose, 1 mg/kg/daily for 7 days, and 10 mg/kg/daily for 7 days. The Fleximer2-leptin preparation (at 10 mg/kg/single dose, 1 mg/kg/daily for 7 days, and 10 mg/kg/daily for 7 days) was tested vs. an Fc-leptin preparation (10 mg/kg/single dose).

Figure 1:
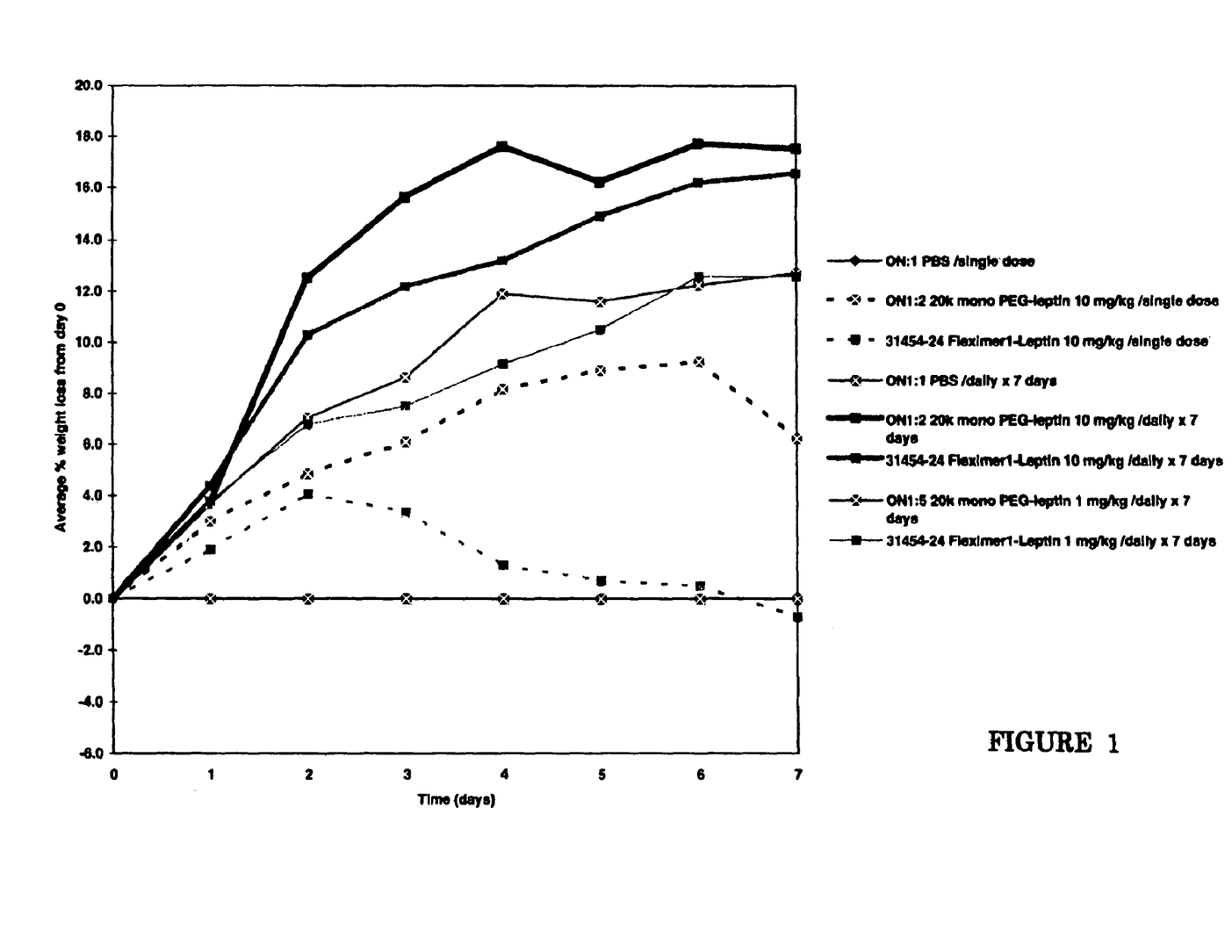
FIG. 1 is a graph depicting single dose induced weight loss percentages for various leptin preparations in a model wherein mice were dosed with either a single subcutaneous injection of 1 mg/kg or 10 mg/kg of each preparation. Percent (%) weight loss is plotted vs. number (#) of days. Percent weight loss is calculated as the difference between test group and buffer control.

As depicted in FIG. 1, the Fleximer1-leptin preparation induced 12%-17% weight loss by day 7 when administered at 10 mg/kg. The 20 kDa monoPEG-leptin preparation was also effective in inducing weight loss in the model.

Figure 2:
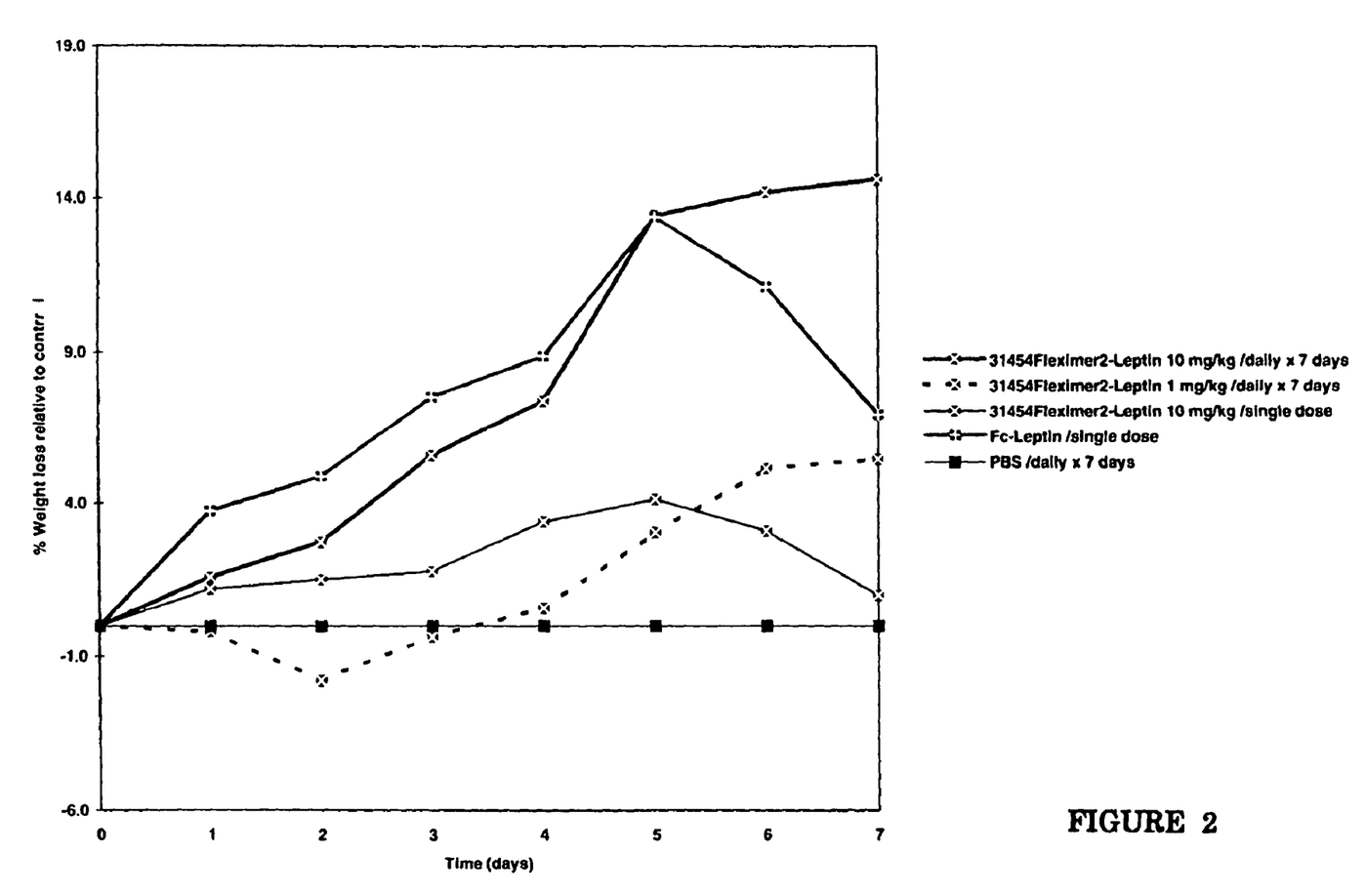
FIG. 2 is a graph depicting single dose induced weight loss percentages for various leptin preparations in a model wherein mice were dosed with either a single subcutaneous injection of 1 mg/kg or 10 mg/kg of each preparation. Percent (%) weight loss is plotted vs. number (#) of days. Percent weight loss is calculated as the difference between test group and buffer control.

As depicted in FIG. 2, the Fleximer2-leptin preparation induced 14% weight loss by day 7 when administered at 10 mg/kg/daily for 7 days. The Fc-leptin preparation was also effective to some extent in inducing weight loss in the model.

EXAMPLE 4

The accumulation of renal vacuoles in the proximal microtubule epithelium has been observed with administration of 20 kDa mono PEGylated-leptin and is dose dependent. Although the doses required to induce vacuoles are well in excess of the therapeutic dose and even severe vacuole induction caused no detectable renal dysfunction, this apparent toxicity is considered undesirable.

In this study, adult (8-12 week-old) female C57BL/6 mice weighing 18-21 g received subcutaneous injections (constant volume of 100 μl) of either buffer (PBS), 20 kDa monoPEG-leptin, Fleximer1-leptin or Fleximer2-leptin. Animals (n=5/group) were dosed according to Table 2:

TABLE 2

| Group No. | Leptin Conjugate | Daily Dose (mg/kg) | Number of Days |
|---|---|---|---|
| 1 | PBS (neg control) | 0 | 7 |
| 2 | 20k mono-PEG leptin | 10 | 7 |
| 3 | Fleximer1-leptin | 10 | 7 |
| 4 | Fleximer2-leptin | 10 | 7 |
| 5 | Fleximer2-leptin | 1 | 7 |
| 6 | Fleximer2-leptin | 10 | 1 |
| 7 | Fc-leptin | 10 | 1 |

The dose was based on mg/kg of protein. Necropsy was performed the day of the last injection, during which spleens and kidneys (n=3/group per organ) were examined for gross abnormalities and then immersed in zinc formalin. Fixed organs were dehydrated in graded alcohols, cleared in Propar, and embedded in paraffin. Both tissues for three mice from each group were processed together. Six-μm-thick sections were stained with hematoxylin and eosin (HE), and multiple fields were examined at 40×, 10× and 400× magnifications. The severity of vacuolar change in renal tubular epithelia and splenic macrophages was graded semi-quantitatively using a five-tiered scale: none, 1+=minimal (rare, small vacuoles), 2+=mild (modest numbers of ~3 μm diameter vacuoles), 3+=moderate (large numbers of ~3 μm to ~5 μm diameter vacuoles), or 4+=marked (>5 μm in diameter vacuoles). Assessments were conducted using a "blinded" paradigm and the results of the study are depicted in Table 3.

TABLE 3

| Group No. | Leptin Conjugate | Daily Dose (mg/kg) | # of Days | Kidney Score | Spleen Score |
|---|---|---|---|---|---|
| 1 | PBS (neg control) | 0 | 7 | None | None |
| 2 | 20K mono-PEG leptin | 10 | 7 | 2+ to 3+ | None |
| 3 | Fleximer1-leptin | 10 | 7 | None | None |
| 4 | Fleximer2-leptin | 10 | 7 | None | None |
| 5 | Fleximer2-leptin | 1 | 7 | None | None |
| 6 | Fleximer2-leptin | 10 | 1 | None | None |
| 7 | Fc-leptin | 10 | 1 | None | None |

The Table 3 data demonstrates that the Fleximer1-leptin and Fleximer2-leptin conjugates did not induce vacuoles in renal epithelium or splenic macrophages of the mice, whereas the 20K mono-PEG leptin was moderately vacuologenic.

EXAMPLE 5

This example describes the preparation of Fleximer1-IL-1ra, Fleximer2-IL-1ra, FleximerG20-Il-1ra, and FleximerG50-IL-ra conjugates. Recombinant methionyl human IL-1ra, prepared as described in the Materials and Methods section below, was used for the conjugations.
Synthesis of Fleximer1-IL-1ra Conjugates Preparation 1: 848.0 mg (49.1 μmol) of IL-1ra (3.685 mL of a 229.9 mg/mL solution) was added to a solution of 442.0 mg (24.6 μmol) of Fleximer1 in 165 mL of maleimide buffer (20 mM phosphate pH 6.5 containing 5 mM EDTA) and stirred in the cold room for 3 days.

Purification 1: A 25 mL aliquot of the reaction mixture was filtered (0.45 μm CA), then dialyzed overnight in two Pierce Slide-A-Lyzer 3.5 cassettes with 2 L of 20 mM NaOAc pH 5.4. The dialyzate was loaded onto a HiLoad 26/10 SP Sepharose HP FPLC column in 20 mM NaOAc pH 5.4 and eluted with a 0.5 M NaCl gradient. Fractions 40-67 were pooled: 336 mL×0.05155 mg/mL=17.3 mg protein.

Purification 2: A 40 mL aliquot of the reaction mixture was filtered (0.45 μm CA), then injected onto the FPLC as described in Purification 1 without prior dialysis. Fractions 18-50 were pooled: 396 mL×0.07521 mg/mL=29.8 mg protein.

Purification 3: A 40 mL aliquot of the reaction mixture was filtered (0.45 μm CA), then dialyzed as per Purification 1. The dialyzate was combined with material from a prior preparation (8.1 mg protein) then injected onto the FPLC as described in Purification 1. Fractions 20-50 were pooled: 372 mL×0.08622 mg/mL=32.1 mg protein.

Purification 4: A 40 mL aliquot of the reaction mixture was processed as per Purification 2. Fractions 10-49 were pooled: 480 mL×0.05239 mg/mL=25.1 mg protein.

Purification 5: A 22 mL aliquot of the reaction mixture plus 5 mL (25.7 mg protein) from a prior preparation was processed as per Purification 2. Fractions 13-49 were pooled: 444 mL×0.03355 mg/mL=14.9 mg protein.

The pools from Purifications 1-5 were combined (2028 mL, 109.2 mg protein) and concentrated in a 400 mL stirred cell with a YM-3 membrane (pre-sterilized with 70% ethanol) to ~50 mL. This material was diafiltered with D-PBS then concentrated to 14.0 mL which was filtered with a Millipore Steriflip Filter Unit (0.22 μm) (7.73 mg/mL=108.3 mg protein). Endotoxin testing (Pyrotell, Associates of Cape Cod, catalog No. GS006) showed >1 and <5 EU/mL. This solution was submitted for in vivo testing.

Synthesis of Fleximer2-IL-1ra Conjugates

Preparation 1: 43.1 mg (2.50 μmol) of IL-1ra (187.4 μL of a 229.9 mg/mL solution) was diluted with 10 mL of maleimide buffer (20 mM phosphate pH 6.5 containing 5 mM EDTA) and then added to a solution of 137.5 mg (1.25 μmol) Fleximer2 in 10 mL of maleimide buffer and stirred in the cold room for 5 days.

The reaction mixture was diluted with 20 mL of D-PBS and filtered through a coarse sintered glass funnel. The filtrate was placed in a 200 mL Amicon stirred cell with a YM-100 membrane and diafiltered vs. D-PBS. The retentate was 38 mL at 0.881 mg/mL=33.5 mg protein.

Preparation 2: 129.3 mg (7.50 μmol) of IL-1ra (562 μL of a 229.9 mg/mL solution) was added to a solution of 412.5 mg (3.75 μmol) of Fleximer2 in 60 mL of maleimide buffer (20 mM phosphate pH 6.5 containing 5 mM EDTA) and stirred in the cold room for 2 days.

The reaction mixture was diluted with 60 mL of D-PBS and filtered through a coarse sintered glass funnel. The filtrate was placed in a 200 mL Amicon stirred cell with a YM-100 membrane and diafiltered vs. D-PBS. A total of 1100 mL of diafiltrate was collected. The retentate, 105 mL at 1.136 mg/mL=106.1 mg protein, was combined with the product from Preparation 1 and concentrated to 31 mL. This solution was diluted to 350 mL with D-PBS and filtered (0.45 μm CA; very slow). The filtrate contains 64.4 mg of protein (350 mL at 0.1839 mg/mL; 49.0% recovery).

Preparation 3: 129.3 mg (7.50 μmol) of IL-1ra (562 μL of a 229.9 mg/mL solution) was added to a solution of 412.5 mg (3.75 μmol) Fleximer2 in 60 mL of maleimide buffer (20 mM phosphate pH 6.5 containing 5 mM EDTA) and stirred in the cold room for 3 days.

The reaction mixture was diluted with 60 mL of D-PBS and filtered through a coarse sintered glass funnel. The filtrate was placed in a 200 mL Amicon stirred cell with a YM-100 membrane and diafiltered vs. D-PBS. A total of 1725 mL of diafiltrate was collected. The retentate was diluted to 500 mL with D-PBS and filtered (0.45 μm CA; very slow). The filtered material contained 58.7 mg of protein (500 mL at 0.1173 mg/mL).

The product from Preparation 3 was combined with the Preparation 1/2 product mixture in a 400 mL stirred cell (pre-sterilized with 70% ethanol; YM-10 membrane) and concentrated to 17.0 mL (6.16 mg/mL=104.7 mg protein). Endotoxin testing (Pyrotell, Associates of Cape Cod, catalog No. GS006) showed ≧10 and <100 EU/mL. This solution was submitted for in vivo testing.

Synthesis of FleximerG20-Il-1ra Conjugates

Preparation 1: 103.0 mg (5.15 μmol) of FleximerG20 was dissolved in 1.03 mL of 100 mM phosphate buffer pH 6.9 and treated with NaIO$_4$ (42.7 μL of a 50.0 mg/mL solution in water; 10.0 μmol) at room temperature in the dark for 30 minutes. The reaction mixture was diluted with 1.82 mL of 100 mM phosphate buffer pH 5.0 and applied to a Bio-Rad PD-6 column in the same buffer. The eluant (~4 mL) was cooled to 4° C., and then mixed with IL-1ra (1.88 mL of a 229.9 mg/mL solution; 432. mg, 25.0 μmol) and sodium cyanoborohydride (318 μL of a 1.0 M solution in water; 318 μmol). The reaction mixture was stirred in the cold room for 26 days while a white suspension slowly formed.

The white suspension was diluted with 6 mL of 20 mM acetate buffer pH 5.4, stirred for 1 hour in the cold and filtered (0.45 μm CA). The filtrate was loaded onto a HiLoad 26/10 SP Sepharose HP FPLC column in 20 mM NaOAc pH 5.4 and eluted with a 0.5 M NaCl gradient. Fractions 5-8 were pooled: 48 mL at 0.642 mg/mL=30.8 mg protein.

Preparation 2: 309.0 mg (15.4 μmol) of FleximerG20 was dissolved in 3.09 mL of 100 mM phosphate buffer pH 6.9 and treated with NaIO$_4$ (128.1 μL of a 50.0 mg/mL solution in water; 30.0 μmol) at room temperature in the dark for 30 minutes. The reaction mixture was diluted with 5.46 mL of 100 mM phosphate buffer pH 5.0 and 3×3 mL applied to three Bio-Rad PD-6 columns in the same buffer. The combined eluants (~12 mL) were cooled to 4° C., and then mixed with IL-1ra (5.64 mL of a 229.9 mg/mL solution; 1296. mg, 75.0 μmol) and sodium cyanoborohydride (954 μL of a 1.0 M solution in water; 954 μmol). The reaction mixture was stirred in the cold room for 34 days while a white suspension slowly formed.

The white suspension was diluted with 18 mL of 20 mM acetate buffer pH 5.4, stirred for 2 hours in the cold and filtered (0.45 μm CA+pre-filter). The filtrate was loaded onto a HiLoad 26/10 SP Sepharose HP FPLC column in 20 mM NaOAc pH 5.4 and eluted with a 0.5 M NaCl gradient. Fractions 5-8 were pooled: 48 mL at 2.63 mg/mL=126.5 mg protein.

The pooled conjugate fractions from Preparations 1 and 2 were combined and concentrated in two Amicon Centriprep YM-10's, then diluted and concentrated twice using D-PBS leaving 14.2 mL at 9.640 mg/mL=136.9 mg protein. GPC analysis showed 0.49% free IL-1ra present; endotoxin testing (Pyrotell, Associates of Cape Cod, catalog No. GS006) showed <10 EU/mL. This solution was submitted for in vivo testing.

Synthesis of FleximerG50 Aldehyde-Il-1ra Conjugates 1.0656 g (21.3 μmol) of FleximerG50 was dissolved in 7.4 mL of 100 mM phosphate buffer pH 6.9, sodium periodate (0.0085 g, 40.0 μmol) and stirred at room temperature in the dark for an hour. The reaction mixture was diluted with 3.44 mL of 100 mM phosphate buffer, pH 5.0. The reaction mixture was divided into four portions and each portion loaded onto a Bio-Rad PD-6 column which was equilibrated with 5 mL of 100 mM phosphate buffer, pH 5.0. Each column was eluted with ~4 mL of the same buffer, and the eluants combined and cooled to 4° C.

Il-1ra (1.7 g, 98 μmol) was added to the FleximerG50 aldehyde solution and the solution was treated with sodium cyanoborohydride (final concentration of 15 mM). The reaction was stirred at 4° C. for 37 days and followed by GPC. The polymer conjugate was purified by FPLC. The reaction mixture was diluted with 20 mM sodium acetate pH 5.4 to 150 ml and filtered through a 0.5 μm membrane. The filtrate was loaded onto a HiLoad 26/10 SP Sepharose HP FPLC column in 20 mM NaOAc pH 5.4 and eluted with a 1.0 M NaCl gradient. Fractions were assayed by SDS-PAGE (4-20% Tri-Gly; visualized with Coomassie Blue) and fractions 30-39 were pooled: 72 mL at 2.2 mg/mL=158 mg protein.

EXAMPLE 6

The in vivo efficacy of the Fleximer1-IL-1ra conjugate, Fleximer2-IL-1ra conjugate, FleximerG20-IL-1ra conjugate, and FleximerG50-IL-1ra conjugate was tested in a rat arthritis model by monitoring paw swelling relative to a HSA and collagen control. Fc-IL-1ra preparations and HSA-IL-1ra preparations were also evaluated.

Study 1. Collagen-induced arthritic (CIA) rats (Lewis Rats; 1 mg collagen/IFA emulsion) were treated with a single subcutaneous injection of 30 mg/kg Fc-IL-1ra, Fleximer1-IL-1ra, Fleximer2-IL-1ra or HSA-IL-1ra on arthritis day 0. The extent of inflammation (paw swelling (mm)) was calculated as increase in ankle joint width compared to arthritis day 0. Kruskal-Wallis ANOVA and Mann-Whitney U test was used to evaluate differences between any two groups. A p value of less than 0.05 was considered significant. Paw swelling was measured for 7 days post onset.

As depicted in Table 4 below, the Fleximer2-IL-1ra preparation and Fc-IL-1ra preparation were most effective in minimizing the extent of inflammation in the CIA rats.

TABLE 4

| | Paw Swelling (mm) | | |
|---|---|---|---|
| Sample | Day 2 | Day 4 | Day 6 |
| Normal | 0 | 0 | 0 |
| Collagen Control | .80 mm | 1.1 mm | 1.45 mm |
| HSA Control | .40 mm | .86 mm | 1.25 mm |
| Fc-IL-1ra | .10 mm | .35 mm | .85 mm |
| Fleximer1-IL-1ra | .35 mm | .91 mm | 1.27 mm |
| Fleximer2-IL-1ra | .23 mm | .63 mm | .88 mm |
| HSA-IL-1ra | .41 mm | .90 mm | 1.27 mm |

Study 2. Collagen-induced arthritic (CIA) rats (Lewis Rats; 1 mg collagen/IFA emulsion) were treated with a single subcutaneous injection of 30 mg/kg, 10 mg/kg, or 3 mg/kg Fc-IL-1ra or Fleximer2-IL-1ra on arthritis day 0. The extent of inflammation (paw swelling (mm)) was calculated as increase in ankle joint width compared to arthritis day 0. Paw swelling was measured for 7 days post onset.

As depicted in Table 5 below, the Fleximer2-IL-1ra preparation and Fc-IL-1ra preparation were both effective in minimizing the extent of inflammation in the CIA rats, with the Fc-IL-1ra preparation at 30 mg/kg being most effective.

TABLE 5

| | Paw Swelling (mm) | | |
|---|---|---|---|
| Sample | Day 2 | Day 4 | Day 6 |
| Normal | 0 | 0 | 0 |
| Collagen Control | .90 mm | 1.6 mm | 2.1 mm |
| PBS Control | .90 mm | 1.5 mm | 2.1 mm |
| Fc-IL-1ra (30 mg) | .30 mm | .45 mm | .60 mm |
| Fc-IL-1ra (10 mg) | .62 mm | 1.0 mm | 1.2 mm |
| Fc-IL-1ra (3 mg) | .60 mm | 1.15 mm | 1.6 mm |
| Flex2-IL-1ra (30 mg) | .65 mm | 1.1 mm | 1.6 mm |
| Flex2-IL-1ra (10 mg) | .60 mm | 1.1 mm | 1.4 mm |
| Flex2-IL-1ra (3 mg) | .70 mm | .90 mm | 2.0 mm |

Study 3. Collagen-induced arthritic (CIA) rats (Lewis Rats; 1 mg collagen/IFA emulsion) were treated with a single subcutaneous injection of 30 mg/kg Fc-IL-1ra or FleximerG20-IL-1ra on arthritis day 0. The extent of inflammation (paw swelling (mm)) was calculated as increase in ankle joint width compared to arthritis day 0. Paw swelling was measured for 7 days post onset.

As depicted in Table 6 below, the FleximerG20-IL-1ra preparation was effective in minimizing the extent of inflammation in the CIA rats.

TABLE 6

| | Paw Swelling (mm) | | |
|---|---|---|---|
| Sample | Day 2 | Day 4 | Day 6 |
| Normal | 0 | 0 | 0 |
| Collagen Control | .80 mm | 1.7 mm | 2.1 mm |
| PBS Control | .70 mm | 1.7 mm | 2.2 mm |
| Fc-IL-1ra | .20 mm | .70 mm | 1.3 mm |
| FleximerG20-IL-1ra | .45 mm | 1.1 mm | 1.8 mm |

Study 4. Collagen-induced arthritic (CIA) rats (Lewis Rats; 1 mg collagen/IFA emulsion) were treated with a single subcutaneous injection of 30 mg/kg Fc-IL-1ra or FleximerG50-IL-1ra on arthritis day 0. The extent of inflammation (paw swelling (mm)) was calculated as increase in ankle joint width compared to arthritis day 0. Paw swelling was measured for 7 days post onset.

As depicted in Table 7 below, the FleximerG50-IL-1ra preparations was effective in minimizing the extent of inflammation in the CIA rats.

TABLE 7

| | Paw Swelling (mm) | | |
|---|---|---|---|
| Sample | Day 2 | Day 4 | Day 6 |
| Normal | 0 | 0 | 0 |
| Collagen Control | .60 mm | 1.3 mm | 1.75 mm |
| PBS Control | .40 mm | 1.2 mm | 1.5 mm |
| Fc-IL-1ra | .15 mm | .40 mm | 1.1 mm |
| FleximerG50-IL-1ra | .25 mm | .65 mm | 1.2 mm |

EXAMPLE 7

PHF was prepared as described above, using dextran B-512 with molecular weight of 188 kDa. PHF (100 mg), succinic anhydride (7.5 mg, 0.075 mmol) and DMAP (1.2 mg, 0.01 mmol) were dissolved in 5 ml of anhydrous pyridine. After 18 hours of incubation at 40° C., pyridine was removed in vacuum, the residue was suspended in deionized water, and the pH was adjusted to 7.0 by addition of 1 N NaOH. The product, succinilated PHF, was purified on Sephadex G-25 with deionized water as an eluent, and recovered via lyophilization. The succinic acid content, as determined by potentiometric titration, was 11.3%. The $^1$H NMR spectrum of the polymer (D$_2$O) contained signals of characteristic methylene protons of succinic acid ester at δ 2.62 (t) and δ 2.46 (t).

PHF-SA-trypsin conjugates: The solution of PHF-SA with Mn 176 kDa (100 mg) in 2.0 mL of deionized water was combined with 3.0 ml of 5.0 mg/ml trypsin solution in 0.1M phosphate buffer pH 7.4. EDC (20 mg) was added to the reaction mixture in 500 uL of cold (0-5° C.) deionized water immediately after dissolution. Trypsin conversion after 3 hours of incubation according HPLC (UV at 280 nm) was 97%. The reaction mixture was purified of low molecular weight products and concentrated to approximately 10 mg/ml on PM-30 ultrafiltration membrane using 0.05 M PBS pH 7.0. The conjugate was separated of residual not bound trypsin by Superose-6 column (Pharmacia) with 0.5M PBS pH 7.0 as a running buffer. The resulting conjugation product was stored frozen at −40° C. SEC analysis of this conjugate has shown Mn 245 kDa, PI 1.8, and peak polymer MW 260 kDa. Trypsin conjugate content estimated by HPLC and spectroscopically at 280 nm was 10.7% wt.

For animal studies, protein conjugates were labeled with [$^{111}$In] after modification of the trypsin portion of conjugates with DTPA. EDC mediated coupling was carried out in aqueous solution at DTPA/EDC/Trypsin lysine residue ratio 500:50:1 at pH 7.5. The product was purified by gel filtration. DTPA to protein molar ratio determined by Cu(II) calorimetric assay at 775 nm was approximately 1:4.

Labeling was performed by transchelation from [$^{111}$In] citrate. The labeling solution was prepared by mixing [$^{111}$In] InCl solution in 0.05 M HCl with 20-fold volume excess of 0.5 M sodium citrate, pH=5.6. The resultant [$^{111}$In] citrate solution was added to unbuffered solution of the DTPA-derivatized conjugate, 0.2 [$^{111}$In] per 1 mg dry substance. The labeled conjugate was separated by gel filtration on Sephadex G-25, with simultaneous buffer replacement to sterile isotonic saline. Labeling efficacy after transchelation estimated by HPLC equipped with gamma detector on average exceeded 90%, and radiochemical purity after desalting was >99%.

Adult male CD1 mice (28 g to 34 g, from Charles River Laboratories, Wilmington, Mass.) were injected IV via the tail vain with 150 μL of $^{111}$In-labeled polymer solution (containing approximately 10 μCi per injection). Mice were sacrificed at 0.25, 0.5, 1, 2, 4, and 8 hours (n=2 per point), blood samples were taken and specified organs (hart, lungs, liver, spleen, kidneys, adrenal glands, stomach, GI, testes, muscle, bone, brain and tail) were harvested and analyzed on gamma counter. The amount of radioactivity was expressed as a percentage of the injected dose per gram tissue.

Unmodified radiolabeled trypsin preparation (control) showed clearance of 80% of activity from blood within 15 minutes after administration (i.e., initial blood half life ca. 7 min), followed by an apparently monoexponential clearance with 4±0.8 hour half-life, where the first (main) phase is consistent with renal clearance and extravasation into interstitial space in various tissues, and the second phase can be related to redistribution back from the tissues and prolong circulation of trypsin complexes with proteins of plasma.

PHF-Trypsin conjugate showed a bi-phasial blood clearance with approximately 40% of activity cleared within 1 hour, the rest (main fraction) remained in circulation with a half-life time of 8 hours, which is consistent with extravasation of the smaller fraction of the unfractionated conjugate, and the second phase is consistent with circulation of the main fraction.

Materials and Methods

The water-soluble polymers contemplated for use are the biodegradable, biocompatible polyacetals described in U.S. Pat. Nos. 5,811,510, 5,863,990, and 5,958,398. A preferred polymer is poly-(hydroxymethylene hydroxymethylformal).

Recombinant methionyl human leptin (rmetHu-leptin) was prepared as described in PCT International Publication Numbers WO 96/05309 and WO 00/21574, each of which is herein incorporated by reference in its entirety. The leptin moieties used herein may be made in prokaryotic or in eukaryotic cells, although, for the leptin moieties used in the working examples below, bacteria is preferred for ease in commercial manufacture. One may further use leptin made in human cells, such as that made by controlling a native or introduced regulatory element which affects the regulation of an endogenous gene encoding the desired protein.

Recombinant methionyl human Il-1ra was prepared as described in e.g., U.S. Pat. No. 5,075,222. One may further use Il-1ra made in human cells, such as that made by controlling a native or introduced regulatory element which affects the regulation of an endogenous gene encoding the desired protein.

EXAMPLE 8

Amino modified carrier was modified with 10 kDa poly (hydroxymethylethylene hydroxymethylformal) (PHF) containing 20% aldehyde groups. The latter polymer was prepared via oxidation of Dextran B512 with 1.8 periodate molecules per carbohydrate ring, with subsequent borohydride reduction and second periodate oxidation of the resultant glycol groups. Aldehydro-PHF (50-fold excess) was reacted with the amino modified carrier core in the presence of cyanoborohydride (1 mole per mole aldehyde) overnight at ambient temperature. The product (oligonucleotide-PHF conjugate) was isolated by SEC HPLC. Both carriers were lyophilized.

EXAMPLE 9

A PHF-modified carrier, analogous in structure to the carrier of Example 8 but comprising glycol groups in the polymer chains, was prepared using a modified technique. The amino modified carrier was modified with 10 kDa poly(hydroxymethylethylene hydroxymethylformal) (PHF) containing 10% aldehyde groups and 10% glycol groups. The latter was prepared by incomplete periodate oxidation of the same polymer as in Example 8 (prepared via oxidation of Dextran B512 with 1.8 periodate molecules per carbohydrate ring, with subsequent borohydride reduction). The carrier (0.1 mg) was treated with 1 ml of 10 mM periodate for 5 minutes, purified on PD-10 column, and conjugated with rabbit anti-fluorescein IgG (0.01 mg) (Molecular Probes, Oreg.) by overnight incubation in the presence of 0.1 mg/ml sodium cyanoborohydride at pH=8, 25° C. The conjugate was separated from the unreacted IgG by HPLC (yield by IgG absorption at 280 nm: 22±9%). The presence of active IgG in the conjugate was determined by quenching of fluorescein fluorescence (10 nM fluorescein, pH=8, 25° C.). The calculated amount of active IgG in the carrier was 10.3% w/w.

What is claimed is:

1. A biodegradable, biocompatible polyacetal derivative derived from controlled lateral oxidative cleavage of dextran, the polyacetal derivative having the structure:

wherein p is an integer;
each occurrence of $R_1$ and $R_2$ is independently hydrogen or —$CH_2OH$; with the proviso that $R_1$ and $R_2$ cannot be both —$CH_2OH$ within the same bracketed structure p;
for m independent occurrences of the bracketed structure p, $R_1$ and $R_2$ are each hydrogen;
for n independent occurrences of the bracketed structure p, one of $R_1$ and $R_2$ is hydrogen, the other is —$CH_2OH$;
the sum m+n=p; and
m:n is within a range achieved when the polyacetal derivative is produced through oxidation of dextran with periodate in a periodate:dextran ratio of 1.8:1.

2. A polyacetal-protein conjugate, wherein said conjugate is obtained by conjugation of a protein with a biodegradable, biocompatible polyacetal derivative which is oxidized prior to conjugation, wherein the biodegradable, biocompatible polyacetal is derived from incomplete oxidative cleavage of dextran and has the structure:

wherein p is an integer;
each occurrence of $R_1$ and $R_2$ is independently hydrogen or —$CH_2OH$; with the proviso that $R_1$ and $R_2$ cannot be both —$CH_2OH$ within the same bracketed structure p;
for m independent occurrences of the bracketed structure p, $R_1$ and $R_2$ are each hydrogen;
for n independent occurrences of the bracketed structure p, one of $R_1$ and $R_2$ is hydrogen, the other is —$CH_2OH$;
the sum m+n=p; and
m:n is within a range achieved when the polyacetal derivative is produced through oxidation of dextran with periodate in a periodate:dextran ratio of 1.8:1.

3. A composition comprising a polyacetal-protein conjugate of claim 2, and a pharmaceutically acceptable carrier.

4. A method of treating inflammation comprising administering an effective amount of a polyacetal-IL-1ra conjugate to a patient in need thereof, wherein the polyacetal-IL-1ra conjugate is derived from conjugation of IL-1ra with the polyacetal derivative of claim 1 or with the oxidized product of the polyacetal derivative of claim 1.

5. A process for preparing a biodegradable, biocompatible polyacetal polyacetal-protein conjugate, said process comprising: (a) providing a polyacetal derivative having the structure:

wherein p is an integer;
each occurrence of $R_1$ and $R_2$ is independently hydrogen or —$CH_2OH$; with the proviso that $R_1$ and $R_2$ cannot be both —$CH_2OH$ within the same bracketed structure p;

for m independent occurrences of the bracketed structure p, $R_1$ and $R_2$ are each hydrogen;

for n independent occurrences of the bracketed structure p, one of $R_1$ and $R_2$ is hydrogen, the other is —$CH_2OH$;

the sum m+n=p; and m:n is within a range achieved when the polyacetal derivative is produced through oxidation of dextran with periodate in a periodate:dextran ratio of 1.8:1;

(b) oxidizing the polyacetal derivative of step (a) to give an oxidized polyacetal derivative;

(c) conjugating the oxidized polyacetal derivative of step (b) to a protein to provide a polyacetal-protein conjugate; and (d) isolating said polyacetal-protein conjugate.

6. A polyacetal-protein conjugate, wherein said conjugate is obtained by conjugation of a protein with a biodegradable, biocompatible polyacetal derivative which is oxidized with periodate prior to conjugation, wherein the biodegradable, biocompatible polyacetal is prepared by oxidation of dextran with a periodate:dextran molar ratio of 1.8:1.

* * * * *